United States Patent
Guirguis

[19]

[11] Patent Number: 6,091,483
[45] Date of Patent: *Jul. 18, 2000

[54] METHOD AND APPARATUS FOR PREPARING SUBSTANCES FOR OPTICAL ANALYSIS

[75] Inventor: Raouf A. Guirguis, Vienna, Va.

[73] Assignee: LaMina, Inc., Herndon, Va.

[*] Notice: This patent issued on a continued prosecution application filed under 37 CFR 1.53(d), and is subject to the twenty year patent term provisions of 35 U.S.C. 154(a)(2).

[21] Appl. No.: 08/836,486

[22] PCT Filed: Nov. 3, 1995

[86] PCT No.: PCT/US95/14528

§ 371 Date: May 5, 1997

§ 102(e) Date: May 5, 1997

[87] PCT Pub. No.: WO96/14563

PCT Pub. Date: May 17, 1996

[51] Int. Cl.[7] .................................................. G01N 21/84
[52] U.S. Cl. ............................................... 356/36; 356/39
[58] Field of Search .................................. 356/38, 36, 39

[56] References Cited

U.S. PATENT DOCUMENTS

| | | |
|---|---|---|
| 536,552 | 3/1895 | Swift . |
| 3,722,502 | 3/1973 | Besuner et al. . |
| 3,774,455 | 11/1973 | Seidler . |
| 3,814,522 | 6/1974 | Clark et al. ........................ 356/246 X |
| 3,851,972 | 12/1974 | Smith et al. . |
| 4,040,791 | 8/1977 | Kuntz . |
| 4,066,359 | 1/1978 | Bucalo ................................. 356/38 X |
| 4,170,056 | 10/1979 | Meyst et al. . |
| 4,395,493 | 7/1983 | Zahniser et al. ..................... 356/38 X |
| 4,435,507 | 3/1984 | Stenkvist . |
| 4,473,530 | 9/1984 | Villareal . |
| 4,557,274 | 12/1985 | Cawood . |
| 4,573,983 | 3/1986 | Annis . |
| 4,609,264 | 9/1986 | Podvin et al. . |
| 4,685,472 | 8/1987 | Muto . |
| 4,827,944 | 5/1989 | Nugent . |
| 4,941,742 | 7/1990 | Schrader et al. ......................... 356/38 |
| 4,960,130 | 10/1990 | Guirguis . |
| 5,016,644 | 5/1991 | Guirguis .................................. 128/771 |
| 5,022,411 | 6/1991 | Guirguis . |
| 5,038,793 | 8/1991 | Guirguis . |
| 5,042,502 | 8/1991 | Guirguis .................................. 128/771 |
| 5,077,012 | 12/1991 | Guirguis . |
| 5,143,627 | 9/1992 | Lapidus et al. . |
| 5,301,685 | 4/1994 | Guirguis .............................. 128/771 X |

FOREIGN PATENT DOCUMENTS

| | | |
|---|---|---|
| 0503128 | 9/1992 | United Kingdom . |
| WO 93/00580 | 1/1993 | WIPO . |

OTHER PUBLICATIONS

Diagnostic Cytology, Nuclepore Corporation, 1–13.
The ThinPrep Processor and The CDS 1000 Cytology Work Station, Cytce Corporation, 1–21.
Goran Ocklind, Optically Eliminating The Visible Outlines Of Pores In Intact Polycarbonate (Nuclepore) Filters, ACTA Cytological, 31: 946–949 (1987).
Wartio Vaara et al., Nature, 238: 407–408 (1972).
James Robb, M.D. et al, Diagnostic Cytopathology, 14:305–309 (1996).
James Linder, M.D., Arch Pathol Lab Med, 121: 282–286 (1997).
Katherine K. Mul et al., CT (ASCP), The ThinPrep Sample Preparation Process–A Matter of Reproducibility.
G.H. Green et al., Nuclepore Membrane Filter Techniques for Diagnostic Cytology of Urine and Other Body Fluids, Medical Laboratory Technology, 30: 265–271 (1973).
Jacalyn L. Papillo et al. B.S., CT (ASCP), Cell Recovery: ThinPrep Method vs. Cytocentrifugatio.
Martha Hutchinson, Ph.D., M.D. et al., A Study of Cell Loss in the Conventional Pap Smear.

*Primary Examiner*—Frank G. Font
*Assistant Examiner*—Tu T. Nguyen
*Attorney, Agent, or Firm*—Foley & Lardner

[57] ABSTRACT

A solid matter collection apparatus and a method for collecting solid matter in a fluid. The apparatus includes a collection site that collects the solid matter at a predetermined density and location that is suitable for exposing the solid matter to electromagnetic spectroscopy.

18 Claims, 5 Drawing Sheets

METHOD AND APPARATUS FOR PREPARING SUBSTANCES FOR OPTICAL ANALYSIS

TECHNICAL FIELD OF THE INVENTION

The present invention is directed to an apparatus and method for collecting and analyzing matter in a fluid.

BACKGROUND OF THE INVENTION

In a wide variety of technologies, the ability and/or facility in separating matter, typically particulate matter, from a fluid is a critical component in the ability to test for the presence of substances in the fluid. For example, laboratories are now able to use infra-red spectroscopy to determine the presence of cancer cells, but the utility of this technique is hampered by the difficulty in sample preparation. Too often, interference associated with sample preparation obscures the target cells to such a degree that the process is not sufficiently reliable, or too costly.

A similar scenario applies to many other fields which involve detection and/or diagnosis, including environmental testing, radiation research, cancer screening, cytological examination, microbiological testing, and hazardous waste contamination, to name just a few.

In all of these endeavors, a limiting factor in the sample preparation protocol is adequately separating solid matter from its fluid carrier (e.g., a variety of fluids, such as physiological, biological and environmental), and in easily and efficiently collecting and concentration the solid matter in a form readily accessible to electromagnetic radiation. For example, it has been reported that infra red technology can be used to differentiate between malignant cells and normal cells. The cells exhibit a characteristic absorbance wavelength which may be used to identify the presence and type of cell and its quantity. The sample preparation processes involves painstakingly isolating the target cells from tissue or body fluids, then passing an infra-red beam through a support which holds the cell sample. In a typical process, the cells must be collected and smeared on a support, such as a microscope slide. The collection and transfer requires some degree of skill, and even then, a cell smear may not be suitable for analysis using infra red technology.

Diagnostic microbiology and/or cytology, particularly in the area of clinical pathology, bases diagnoses on a microscopic examination of cells and other microscopic analyses. The accuracy of the diagnosis and the preparation of optimally interpretable specimens typically depends upon adequate sample preparation.

The present invention is based in part on the relatively new development of using electromagnetic radiation, such as infrared radiation, to characterize matter. For example, an infra red beam may be passed through some type of support which holds solid matter, such as cells, in a predetermined position. By passing the beam through the solid matter, the solid matter absorbs a characteristic wavelength within the beam; this absorbance can be measured. This measurement, and the characteristic absorbance pattern may be used to identify the type and quantity of the solid matter present in the sample and its molecular make-up or composition.

As noted above, however, any electromagnetic protocol is limited by the manner in which the sample is prepared. The present invention provides an easy, quick, cost efficient, reproducible, and superior process and apparatus for collecting the solid matter suitable for analysis using electromagnetic radiation.

The present invention provides a stark contrast to the various sample preparation techniques typically used. In the cast film method, the sample is dissolved in a solvent, the solution is added dropwise to an infra red window material (KBr or CsI), and the solution is allowed to evaporate, forming a thin film on the window material. In some cases, the thin film must be removed from the window material and placed on an inert solid support prior to exposure to infra red radiation.

In the hot press film technique, polymeric samples are carefully melted between two infra red salt plates (KBr or CsI), carefully pressing one of the plates against the other until a thin film is formed. In a similar technique, a liquid smear is formed by pressing a viscous fluid sample until a capillary film is produced.

In the potassium bromide pellet technique, the sample is ground to a particle size of about one micron, the sample is mixed with infra red grade KBr (carefully, to insure homogeneity), and the powder mixture is pelletized using high pressure.

Low concentration samples may also be prepared using pyrolysis, e.g., forming a dry distillation of a liquid distillate.

It should be readily apparent that for each of these infra red analysis sample preparation protocols, significant manipulation of the sample is required. Furthermore, the sample must be transferred to a solid support or window material (KBr, CsI, glass, aluminum foil, or a mercury surface), materials which sometimes interfere with the sample absorbance pattern.

SUMMARY OF THE INVENTION

The present invention relates to an apparatus and method for collecting matter for detection, analysis, quantification, and/or visualization using electromagnetic radiation. The devices and methods of the present invention are particularly suitable for separating matter from biological, physiological, and environmental fluids and analyzing the particulate matter with infra red radiation. For example, a device according to the invention prepares matter in the sample for analysis, in combination with facilitating the actual application of electromagnetic radiation to the collected matter. Thus, matter is readily analyzed and quantified.

Furthermore, sample collection, isolation, preparation, and analysis may be conducted in a single device. The devices of the present invention obviate the need for a trained technician to properly prepare a sample substrate. Thus, time, expense, and expertise are eliminated or reduced as critical factors in sample preparation protocols.

The devices and methods of the present invention also provide advantages in sample preparation because they are suitable for use with fresh, untreated cells, unmodified cells, and are particularly designed to provide a thin, uniform layer of solid matter (up to approximately 40 microns or more).

Furthermore, the devices and methods of the present invention do not require any manipulation of the collection site or solid support in order to properly expose the captured matter to electromagnetic radiation. This is in contrast to the existing methods of infra red spectroscopy, where the solid support, such as a membrane, must be removed from its housing, the matter must be fixed on another support, such as a microscope slide, and then the support must be properly positioned in a holder.

The devices of the present invention may also be disassembled to allow access to the matter capture medium, thus facilitating additional tests, if they are necessary. For example, after subjecting cells to infra red spectroscopy, the device may be opened, the membrane containing the cells may be removed, and the cells may be fixed on a microscope slide, or may be further processed, such as culturing or hemolyzing the cells, both of which process the cells for further testing.

According to another aspect of the present invention, the matter collection apparatus may also include additional modules, removable or integrated, for treating the fluid. For example, the fluid may be treated with a matter collection module, in combination with a debris removal module, a chromatography module, and assay module, or combinations of these and other devices. These and other modules or treatment protocols provide features which may be desirable to incorporate into a sample preparation apparatus according to the invention.

New methodologies, such as immunocytochemistry and image analysis which may involve tagging target cells with chromophores, or light absorbance or emitting probes, require preparations that are reproducible, fast, biohazard-free and inexpensive. The solid matter preparation techniques of the present invention address the issues of non-uniform matter densities, uneven matter distribution, and sample loss due to the number of steps involved in the sample preparation. The preparations of the present invention result in an even distribution of solids that have superior morphology, improved visualization, and are readily positioned and available for light absorbance analysis without the need to further manipulate or prepare the sample.

For example, these methods have many advantages for conventional microbiology and hematology. The collected cells are in a predetermined area easily accessible to a radiant light source and to a wavelength absorbance meter. Because cells are concentrated in a single layer, they are almost always in one focal plane, thus eliminating or reducing interference by other particles and virtually eliminating technician time and expertise in establishing a proper reading. The apparatuses of the present invention even permit the use of automated devices to detect and analyze any solid matter in a given population. It also permits a detailed analysis of the chemical composition of the matter.

The minimal matter overlap achieved in this process ensures that all matter can be easily examined with little chance for critical solids to be obscured by clumps of overlapping solids or debris.

The accompanying drawings show illustrative embodiments of the invention from which these and other of the objectives, novel features and advantages will be readily apparent.

DETAILED DESCRIPTION OF THE INVENTION

Figure 3:
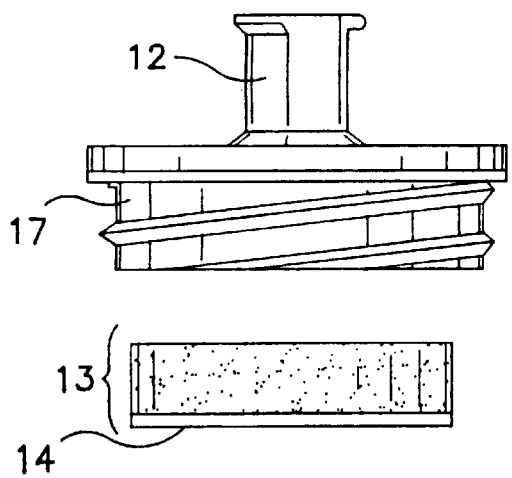
FIG. 3 is a cross section of a collection element according to the present invention, including the collection site and an optical channel.
Figure 3:
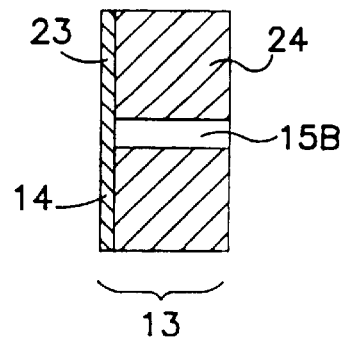

The present invention comprises an apparatus having a housing, a matter collection element disposed in the housing, and an optical channel for providing communication between a radiant energy source and the matter collection element.

The present invention also comprises an apparatus for preparing a sample for exposure to a radiant energy source having a collection site through which the absorbance pattern of the collected matter may be determined.

The present invention also includes collecting fluids, such as biological, physiological, or environmental fluids, removing the desired matter from the fluid, without centrifugation, and diagnosing and testing the matter by applying radiant energy to the matter in the device.

The present invention also includes a method for analyzing matter comprising collecting matter on a collection element, and exposing the collected matter to a radiant energy source. Preferably, the collection step and the exposure step occur within the same housing. A method according to the invention may also include detecting and/or quantifying the absorbance of the radiant energy by the matter, may further include detecting and/or identifying the matter by its characteristic absorbance pattern, and may include determining the composition of the collected sample.

The present invention also includes an automated method for determining the presence and/or amount of a predetermined matter in a fluid.

The present invention also includes a kit having an assay module which includes a matter collection element according to the invention, a fluid specimen cup, and a pump for inducing fluid flow through the assay module.

The present invention also includes a solid matter collection element having a supported collection site and a channel through the support for exposing the collection site to electromagnetic radiation.

In a preferred embodiment of the invention, a collection module collects and concentrates solids in a fluid in a predetermined position and at a predetermined thickness. In this way, the solids may be easily and reproducibly subjected to electromagnetic radiation in order to identify and quantify the captured solid matter.

As used herein, fluid refers to any fluid for which it may be desirable to collect a component of the fluid for the purpose of establishing its identity or presence in the fluid. Typically, the component in the fluid will be a solid matter, such as particulate matter. For example, the fluid may be air or gas, or a biological fluid, such as urine, and it may be desirable to determine the presence of cancer cells or certain proteins in the biological fluid. In another example, it may be desirable to evaluate the nature of contaminants, such as molecular contaminants, in ultra-pure water used in the electronics industry. Other exemplary fluids include but are not limited to other body fluids, such as blood, spinal fluid, or amniotic fluid; bronchial lavage; sputum; fine needle aspirates; ground water; industrial processing fluids; electronic or medical dialysis fluids; to identify just a few. It is intended that the invention should not be limited by the type of fluid being processed.

As used herein, solid matter refers to any substance in a fluid which is capable of collection and evaluation using radiant energy sources. Exemplary matter includes, but is not limited to cells or cell fragments, proteins, molecules, polymers, rubbers, stabilizers, antioxidants, accelerators, silicones, alkyds, thiokols, paraffins, thermoplastics, bacteria, pesticides, and herbicides. Specific exemplary polymeric matter include, but is not limited to polyethylene, polypropylene, polyisobutylene, polyacrylonitrile, polyethylene glycol, polyvinylchloride, polystyrene, polysulfide, polymethylmethacrylates, polyethyleneterephthalates, bisphenol A (a common environmental contaminant), ethyl cellulose, nitrocellulose, polyurethane, and nylon. Specific exemplary biological matter includes cancer cells, including distinguishing between metastatic and normal cancer cells; proteins, nucleic acids, antibodies, or the like. It is intended that the invention should not be limited by the type of matter being processed.

As used herein, electromagnetic radiation refers to radiant energy which can be absorbed by solid matter, including but not limited to infra-red radiation, near infra-red radiation, the visible spectrum, and near ultraviolet radiation. For example, electromagnetic radiation may be used to determine structure, stereo-chemistry, types of additives, degree of degradation, presence of a copolymer, chain length, orientation, crystallinity, carbon-hydrogen stretching region, distinguishing between unsaturated and saturated carbon-hydrogen absorptions, and the presence of individual molecules. Electromagnetic radiation may also be used to determine the composition of a sample, e.g., the composition of a specific cell, protein, molecule, or polymer. It is intended that the invention includes the use of any type of energy which can be used to identify and/or quantify solid matter.

As used herein, adapted for communication, communicating, or the like refer to any means or methods for establishing fluid flow through the system, as are well known by practitioners in the art. A well known structure for establishing communication is a luer lock.

The systems and devices of the present invention are particularly suited to fluids and matter in the fluids which are susceptible to radiant energy evaluation. For example, cancer cells in urine may be identified by measuring the absorbance pattern after exposing the collected cells to infra-red radiation.

An apparatus or assay module according to the invention includes a housing, an inlet and an outlet defining at least one fluid flow path through the housing, and a collection element disposed in the housing across a fluid flow path. In accordance with the invention, the collection element includes a collection site. Although it may be variously configured, as noted in more detail below, the module also includes an optical channel that permits communication between a radiant energy source, such as an infra-red spectrometer, the collection site, and an absorbance meter.

Exemplary methods and apparatuses according to the invention will now be described in reference to the Figures.

Figure 1:
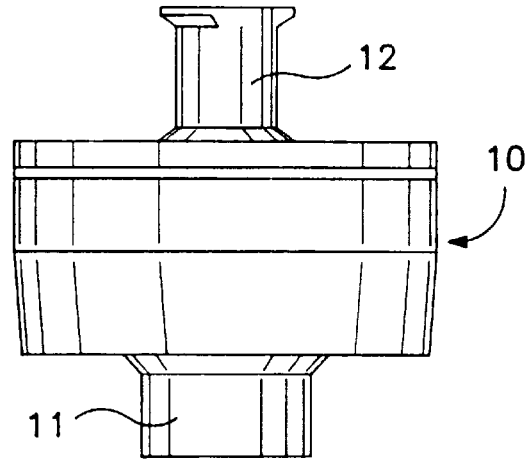
FIG. 1 is a perspective view of a matter collection apparatus according to the present invention.

FIG. 1 shows a typical module according to the invention, each module having a housing 10, an inlet 11, an outlet 12, and a collection element 13 (see FIG. 3).

Figure 2:
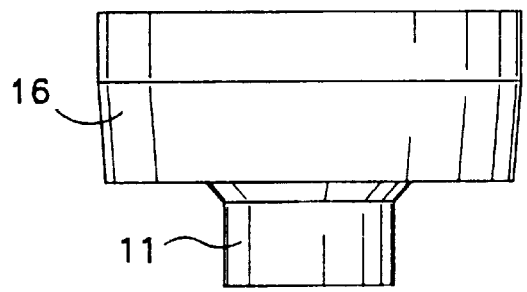
FIG. 2 is an exploded perspective view of a matter collection apparatus according to the, present invention.
Figure 4:
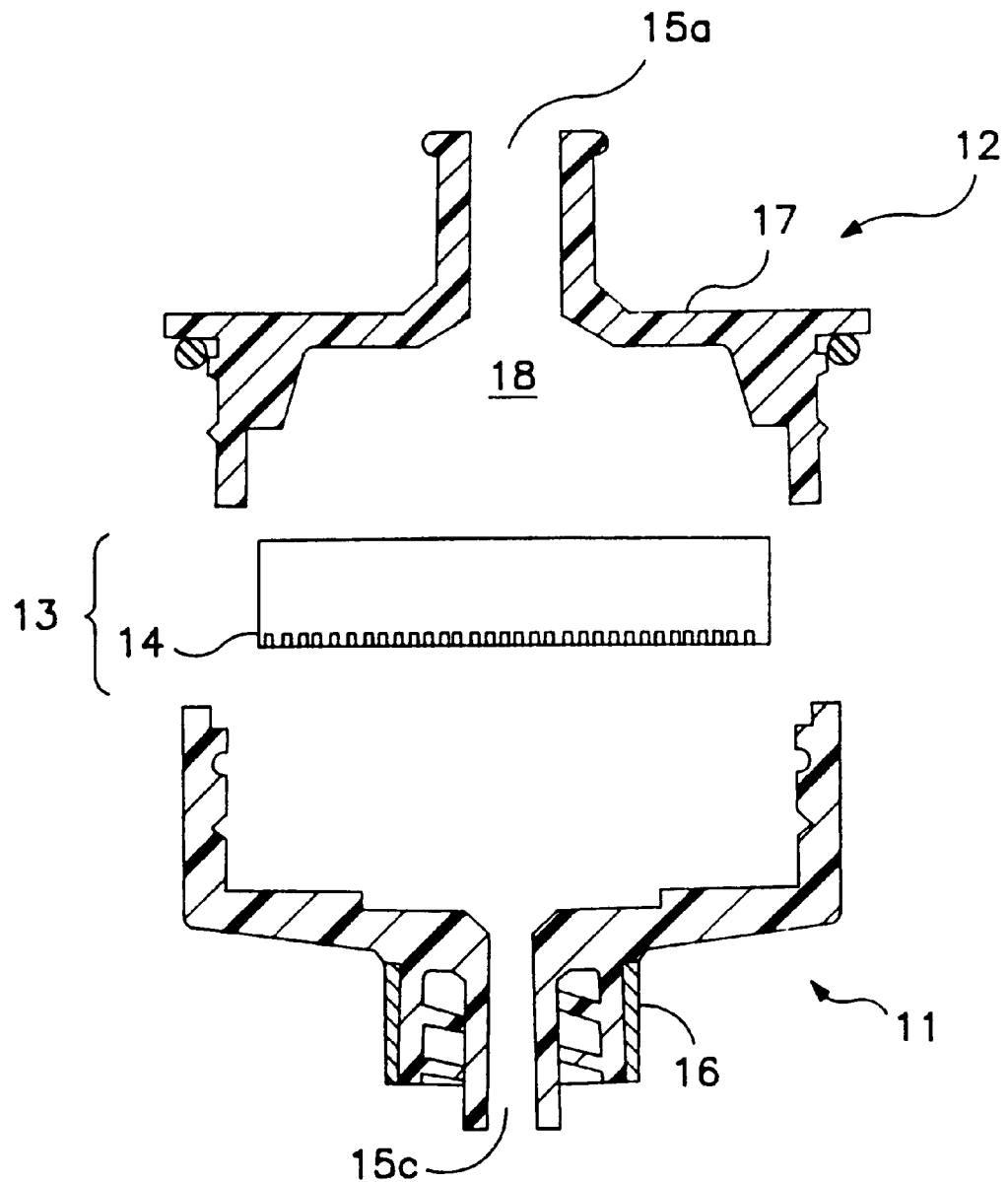
FIG. 4 is an exploded cross section view of a matter collection apparatus according to the present invention.

As shown in FIGS. 2–4, an assay module or matter collection apparatus comprises a housing 10 having an inlet 11 and an outlet 12. The housing 10 defines a chamber 18, and the inlet 11 and the outlet 12 define at least one fluid flow path through the housing 10. A collection element 13 having a collection site 14 adapted to collect matter may be positioned across a fluid flow path, the collection site 14 communicating with the inlet 11. The collection element 13 within the matter collection apparatus is preferably adapted to define a flow path having first and second branches, the first branch 21 extending through the collection site 14 and the second branch 22 bypassing the collection site 14.

In a preferred embodiment, the invention includes a collection element 13 having a first porous medium 23, suitable for preventing the passage of matter therethrough, and a second porous medium 24, suitable for allowing fluid to pass therethrough. The second porous medium may or may not be capable of removing particulate matter from the fluid, a design choice according to the needs of a particular device. In a preferred embodiment, the first porous medium is suitable for capturing or collecting solid matter, and even more preferably, capturing or collecting solid matter in a uniform or single layer. A preferred embodiment also includes a second porous medium which is suitable as a support for the first porous medium.

The collection element 13 also includes an optical channel 15b which allows electromagnetic radiation to contact first porous medium 23 without contacting second porous medium 24. Optical channel 15a, 15b, and 15c is any optical pathway through the module or housing which allows the electromagnetic radiation to contact the solid matter. As illustrated in FIG. 3, the optical channel 15b is a channel, hole, or the like of any shape through the second porous medium, e.g., a centrally positioned annular hole.

The first porous medium and the second porous medium may be positioned in any fashion that functions as described herein. As one skilled in the art will recognize, the collection element may be variously configured and positioned as needed to achieve a particular result. For example, the first and second porous media may be separate, spaced apart media; the two media can be laminated together; the first medium can be integral with or removably engaged with the second porous medium; or the collection element may comprise a zone of higher density which mimics the function of the first porous medium as described above, and zone of lower density which mimics the function of the second porous medium as described above. Choice of these various configurations are well within the skill of practitioners in the art.

In a preferred embodiment of the invention, the first porous medium is a polycarbonate membrane and the second porous medium is a depth filter.

It should be noted that various types of first and second porous media can be used. U.S. Pat. No. 5,301,685 discloses several porous media which may used in the present invention, and are hereby incorporated by reference. While a polycarbonate membrane is especially suitable for use in the solid matter collection apparatus of the present invention, any membrane or septum which does not interfere with the electromagnetic reading protocol is suitable. For example, polycarbonate membranes as well as other porous membranes, such as cellulosic or nylon membranes, are also suitable because these membranes are compatible with infra red spectroscopy protocols. Exemplary media which may be used for fluid screening include LEUCOSORB™, a leucocyte retention medium manufactured by Pall BioSupport Division of Pall Corporation. Other membranes manufactured and sold by the Pall Corporation are BIODYNE A™, an unmodified nylon with surface chemistry 50% amine and 50% carboxyl group which has an isoelectric point of pH 6.5; BIODYNE B™, a surface-modified nylon with surface chemistry characterized by a high density of strong cationic quaternary groups (the zeta potential is positive to pH>10); BIODYNE C™, a surface-modified nylon with surface chemistry characterized by a high density of anionic carboxyl groups (the zeta potential is negative to pH>3; and LOPRODYNE™, a low protein binding nylon 66 membrane with a tightly controlled microporous structure having high voids volume for rapid, efficient throughput of liquids and absolute retention of microparticles designed for cell separation and bacterial cell immunoassays. In a preferred embodiment, the first porous medium is a polycarbonate membrane suitable for preventing the passage of cells therethrough. Preferred polycarbonate membranes are commercially available from Nucleopore, and are well known to those skilled in the art.

The collection element 13 may further include a depth filter as the second porous medium 24. The second porous medium permits fluid to pass through by means of second fluid flow path 22, and may also function as a support for the first porous medium. The depth filter 24 may be made of polypropylene or high density polyethylene POREX® porous plastics, as well as any other material suitable for supporting the first porous medium.

Figure 6:
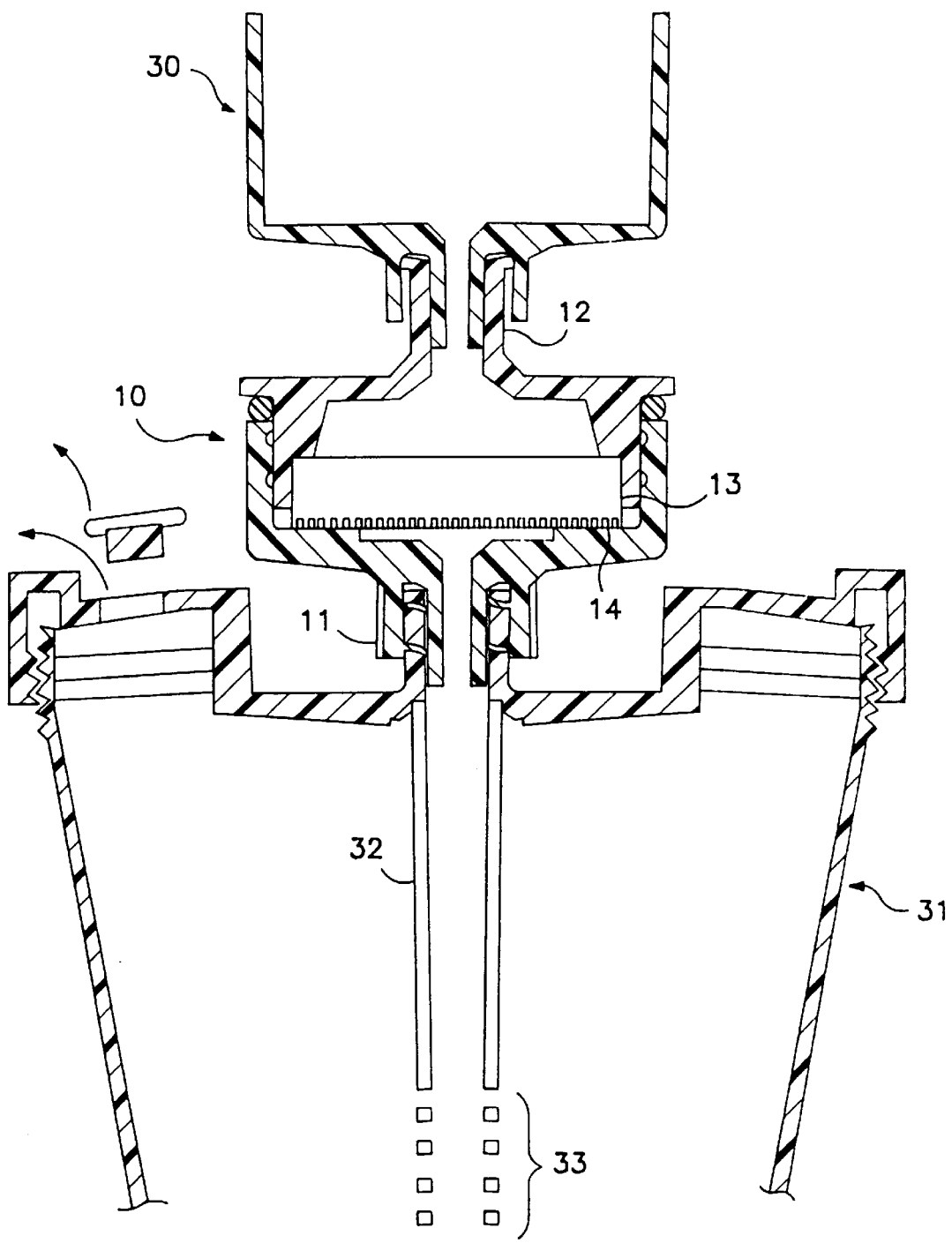
FIG. 6 is a cross section view of a syringe and matter collection apparatus mounted on a collection cup.
Figure 7:
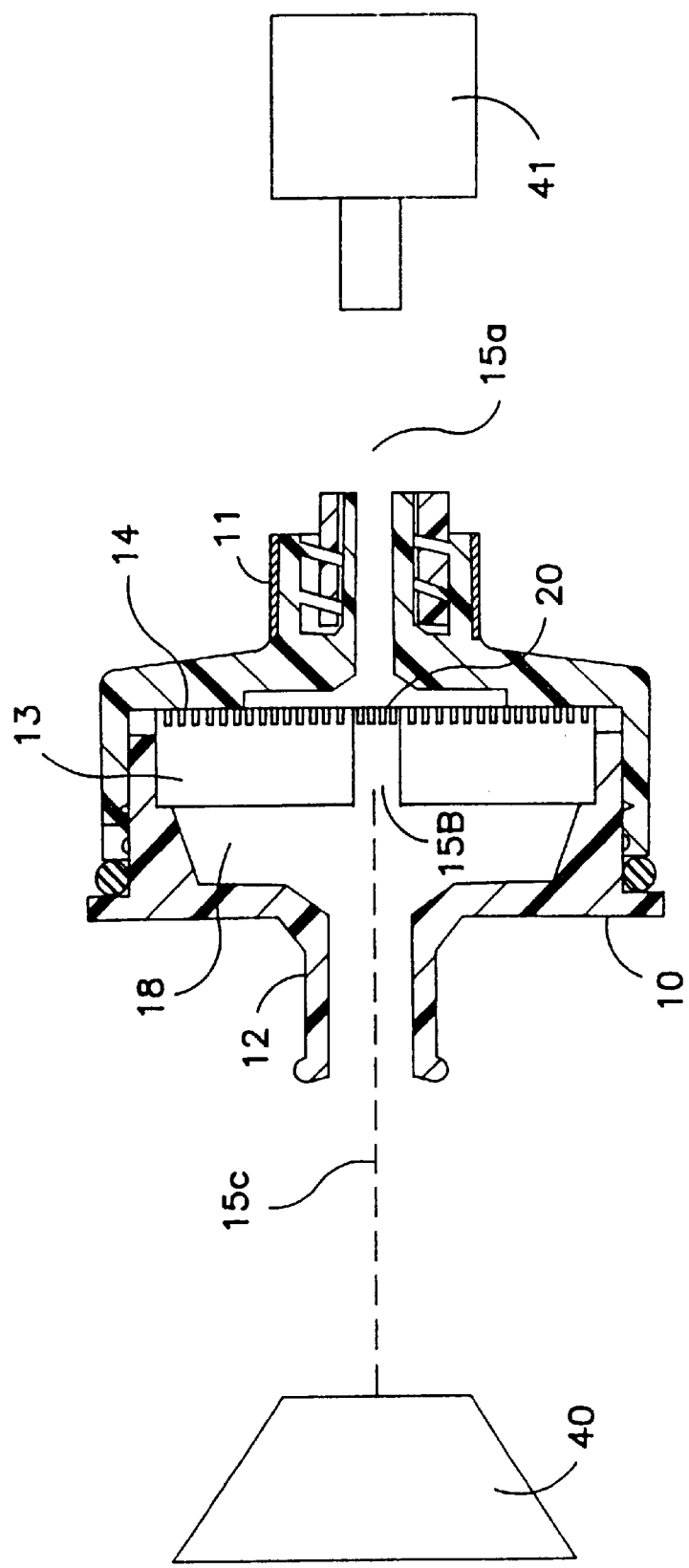
FIG. 7 is a representation of a matter collection and detection system according to the present invention.

As shown in FIGS. 1 and 6, the first portion 16 or inlet 11 may include a portion configured as a connector and may be adapted to connect to a container or the like, or may be configured as a needle or cannula 32 or the like. Second portion 17 or outlet 12 may include a portion configured as a connector and may be adapted to connect to a pump 30, e.g., a syringe, or the like.

The porous membrane preferably has a pore size from about 0.22 microns to about 8 microns, more preferably from about 1 micron to about 6 microns, most preferably about 2 microns, which allows it to trap cells which are more than 3 microns in size. The membrane, is suitable to allow fluid flow to pass therethrough while preventing the passage of particulate matter 20. The second porous medium is suitable for passing fluid therethrough and may also be capable of removing particulate matter from the fluid. The pore size of the second porous medium may range from about 5 microns to about 60 microns, preferably from about 15 microns to about 45 microns, most preferably about 35 microns.

Another embodiment of the invention, illustrated in FIG. 6, includes an assay module or matter collection apparatus 10 mounted on a collection cup 31, and includes a pump 30 for inducing fluid flow through the collection module. The collection cup 31 may be a specimen cup or the like, and/or the pump 30 may be a syringe or any other device for establishing fluid flow. As shown in FIG. 6, either the collection cup 31 or the collection module may include a cannula 32 or the like for drawing fluid from the collection cup into the housing 10. In a preferred embodiment, the cannula includes perforations 33 at various positions along the cannula in order to draw fluid from different levels in the collection cup 31.

The assay module housing 10 may be of any design which permits fluid flow through or across the collection element, e.g., a unitary housing. As shown in the Figures the assay module housing 10 is preferably a two piece housing with a first detachable portion 16 and a second detachable portion 17, although any housing providing access to the collection element 13 is suitable.

Movement of a fluid through the system may be effected by maintaining a pressure differential between a source of fluid and a destination of the fluid. Exemplary means of establishing this pressure differential may be by applying pressure to any part of the system on the inlet side of the housing (e.g., the collection cup); applying a vacuum to any part of the system on the outlet side of the housing (e.g., the syringe); or any form of pump, such as an autovial spunglass filter (manufactured by Genex Corporation); gravity head; or a flexible, collapsible container, such as a specimen container, which may be squeezed to force fluid through the matter collection apparatus and into the syringe. In a preferred embodiment of the invention, a syringe draws fluid from a collection cup through the housing.

Figure 5:
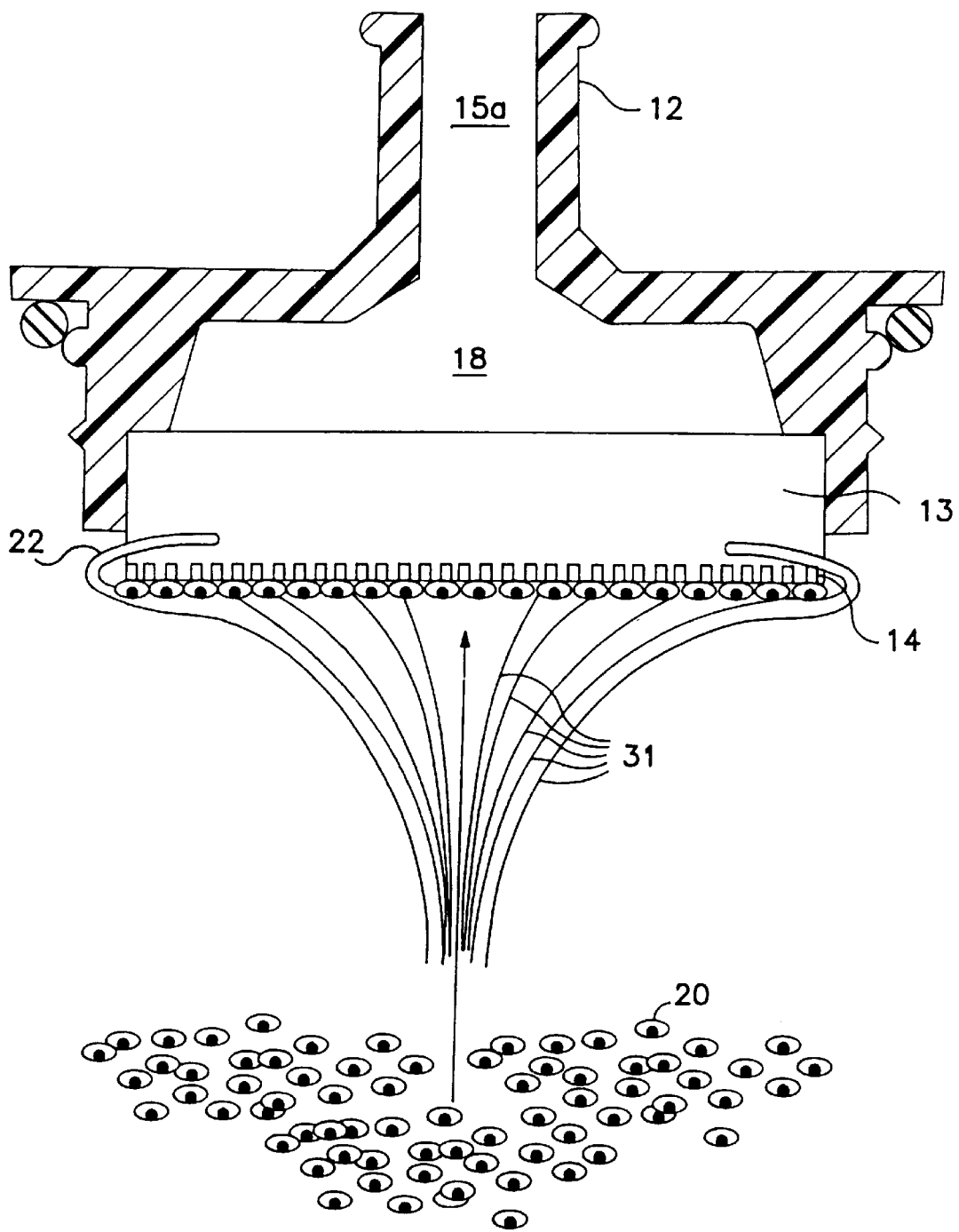
FIG. 5 is a cross section of the outlet portion of a matter collection apparatus showing the flow path of matter and fluid through the collection element.

As fluid passes through housing 10, the fluid flows through collection site 14 and collection element 13, as shown in FIG. 5. As one skilled in the art will recognize, adjusting the pore size of the porous membrane and the porous depth filter in accordance with the type and/or size of matter to be collected permits the collection of the matter on the collection site 14. In a preferred embodiment of the invention, the pore size is chosen so that a uniform layer of matter, preferably a monolayer of matter, is formed on the collection site.

One skilled in the art will also recognize that the depth of the layer may be adjusted to a predetermined or desirable depth. For example, from about 3 $\mu$m to about 40 $\mu$m or more has been shown to be effective, but it is intended that the invention should not be limited to a certain range of size or depth.

Once the uniform or monolayer of matter is formed, fluid flow along a first flow path 21 is reduced in the center of the porous membrane and fluid flow along a second flow path 22 increases towards the edges of the collection element 13. While not intending to be restricted to any theory of operation, it is believed that the increase in the fluid flow path 22 may be due to the blockage of fluid flow path 21 by the collected matter as it collects on the collection site 14. Matter in the second fluid flow path 22 will then bypass the collection site 14, thus maintaining a substantially uniform layer or monolayer on collection site 14. The second fluid flow path 22 passes through an extended side area of the collection element 13, acts as a vent (with low resistance to flow) and which prevents the piling up of matter.

The matter collection apparatus or module described above may be used in combination with other suitable filtration or treatment devices. Exemplary devices include other debris and/or assay devices or modules which may be attached to housing 10. Typically, these additional modules will include a housing having an inlet and an outlet, and will include a filtration, assay, or detection element positioned across the fluid flow path in the housing. For example, the apparatus may comprise a housing including inlet and outlet ports defining a flow path between the inlet and the outlet; a filter positioned across the flow path; and a freely movable chromatography/assay element, such as substrate beads, positioned on the outlet side of the filter. The chromatography/assay element can freely mix with the matter in the fluid, capture the matter, and can then be assayed for the presence of the matter. Suitable devices include those disclosed in U.S. Pat. Nos. 4,953,561; 5,224,489; 5,016,644; 5,139,031; 5,301,685; 5,042,502; and 5,137,031, all incorporated herein by reference.

In accordance with a method of the present invention, matter is collected on a collection element which includes an optical channel for exposing collected matter to electromagnetic radiation. After the matter is collected, the matter is analyzed by passing electromagnetic radiation through the optical channel and then measuring the amount and/or type of absorbance.

For example, fluid may be drawn from a collection cup 31, through housing 10, allowing matter in the fluid to collect in a uniform layer or a monolayer on collection site 14. Optionally, additional fluid may be drawn through the housing, or the same fluid may be drawn, then returned to collection cup 31, and then drawn again, as many times as desirable. Once the matter is collected, the housing 10 may be placed in a holder or the like to properly position the optical channel in the electromagnetic radiation beam, e.g., an infra red beam. The beam passes through the outlet 12 along optical channel 15a, 15b, and 15c. In optical channel 15b, the beam will contact matter collected on the collection site 14. The collected matter absorbs a certain wavelength of the radiation, and this absorbance may be measured by placing an absorption meter in the path of optical channel 15c.

A method according to the invention may also include processing the matter as noted above, and then transferring the matter to another medium for further analysis. For example, the present invention may also include transferring cells to a microscope slide. In contrast to currently available methods, the use of membrane filtration provides a method of depositing cells or other matter evenly over a slide with minimal overlap. This allows for clear observation and optimal diagnostic accuracy.

Included within the scope of the present invention is the production of multiple specimens from a single patient or source sample.

Also, captured microorganisms can be cultured in culture medium such as a standard petri dish. After the layer of cells has been collected in the collection apparatus 10, fluid may be passed through the collection site 14 toward inlet 11 thereby transferring the microorganisms to the petri dish.

In bacteria testing, the collection site 14 can be used for culturing with a Qualture device (not shown) to determine the presence of specific bacteria colonies. The Qualture device is a plastic capsule containing a filter membrane and four nutrient pads of dehydrated, selective media.

The devices and methods of the present invention have a wide variety of uses and applications, primarily because so many industries and so many processes involve the separation of solid matter from a fluid followed by some type of examination of the solid matter. Exemplary industries include food and beverage, pharmaceutical, medical and environmental (e.g., water, soil or air sampling), biology, microbiology, hematology, cytology, and pathology.

The devices and methods of the present invention are particularly useful in any procedure which involves spectroscopy, the identification of solid matter such as compounds, molecules, cells, or proteins singly or in mixtures according to the matter's ability to absorb radiant energy at a specific wavelength. The devices and methods of the present invention are even more useful in any procedure which involves the study of absorption patterns when substances are exposed to electromagnetic radiation in the infra-red region of the spectrum, especially in the wavelength from about 2.5 $\mu$m to about 15 $\mu$m.

For example, in a hematological analysis, a drop of blood may be analyzed for the presence and quantity of certain cell populations, since every cell has a certain signature profile under radiation such as infra red radiation. For example, it may be desirable to determine the ratio of lymphocytes to leukocytes, the presence and type of cancer cells, protein level, or fat level.

In a variety of industries, it may be desirable to determine the presence of a contaminant in a fluid such as air or water, e.g., contaminants in drinking water, or bacteria in food and beverage processing plants. In environmental analysis, it may be desirable to determine the presence, type, and amount of a certain contaminant, such as estrogenic compounds, pesticides (DDT, heptachlor, and atrazine), aromatic hydrocarbons, and polychlorinated biphenyls. In both the medical and environmental fields it may be desirable to determine the presence of breakdown products such as bisphenol-A, an ingredient in plastics.

The devices and methods of the present invention are also particularly useful when the matter may be tagged with a chromophore, a light absorbing or emitting probe, or any other visualization reagent. For example, cells and DNA may be analyzed by using a probe which specifically binds (indirectly or directly) with the matter of interest, and combining that probe with the first porous medium or by mixing the probe with the fluid sample.

It should be clear that the device and method of the present invention may be used in a wide variety of industries, and for determining the presence, amount, and composition of virtually any solid matter.

Although the present invention has been described in terms of a particular preferred embodiments, it is not limited to those embodiments. Alternative embodiments, examples, and modifications which would still be encompassed by the invention may be made by those skilled in the art, particularly in light of the foregoing teachings. Therefore, the following claims are intended to cover any alternative embodiments, examples, modifications, or equivalents which may be included within the spirit and scope of the invention as defined by the claims.

I claim:

1. A solid matter collection apparatus, comprising:
   a housing having an inlet and an outlet, said inlet and outlet defining at least one fluid flow path through said housing;
   a solid matter collection element positioned in the housing across said path, said collection element having a collection site adapted for collecting solid matter from the fluid flow, and an optical channel through which radiant energy from a source of electromagnetic radiation is adapted for irradiating the collection site.

2. The solid matter collection apparatus according to claim 1 wherein the collection element is adapted to define a flow path having first and second branches, wherein the first branch extends through the collection site and the second branch bypasses the collection site.

3. The solid matter collection apparatus according to claim 2 wherein the collection site includes a first porous medium capable of preventing the passage of solid matter therethrough, said porous medium being positioned across the optical channel.

4. A solid matter collection apparatus according to claim 3 wherein the collection site comprises a porous membrane.

5. A system for collecting and analyzing solid matter, comprising:
   source of electromagnetic radiation;
   a solid matter collection module comprising a housing and a collection element, the collection element having a collection site disposed in the housing; and
   an absorbance meter;
   wherein said system includes an optical pathway which passes from the source of the electromagnetic radiation through the collection site to the absorbance meter.

6. The system according to claim 5 wherein the source of electromagnetic radiation is a source of infra red radiation.

7. A solid matter collection element, comprising:
   a porous support having an optical channel through the porous support; and a collection site disposed on the porous support and extending across the optical channel, said collection site being adapted for collecting solid matter at a predetermined density and position on the collection site, wherein collected matter will be in the path of electromagnetic radiation passing through the optical channel.

8. The solid matter collection element according to claim 7 wherein the porous support is a depth filter.

9. The solid matter collection element according to claim 7 wherein the collection site comprises a membrane.

10. The solid matter collection element of claim 9 wherein the membrane has a pore size from about 0.3 microns to about 35 microns.

11. A method of analyzing solid matter in a fluid, comprising:

screening the solid matter from the fluid and collecting the solid matter on a collection site;

exposing collected solid matter to electromagnetic radiation passing through the collection site; and analyzing the solid matter exposed to the electromagnetic radiation.

12. The method according to claim 11, wherein said separating solid matter from the fluid and collecting the solid matter on the collection site comprises passing the fluid through a collection element having the collection site whereby solid matter in the fluid is separated from the fluid and collected in a uniform layer on the collection site.

13. The method according to claim 11, wherein said exposing the solid matter to electromagnetic radiation comprises exposing the solid matter to infrared radiation.

14. The method according to claim 11, wherein said analyzing the solid matter exposed to the electromagnetic radiation comprises identifying the solid matter present on the collection site.

15. The method according to claim 14, wherein identifying the solid matter present on the collection site includes quantifying the solid matter present.

16. A method for preparing solid matter for infra red spectroscopy, comprising:

a) passing a fluid containing the solid matter through a collection apparatus that includes a collection element having a collection site adapted for collecting the solid matter and an optical channel through the collection element adapted for exposing the solid matter on the collection site to infra red radiation; and b) depositing a uniform layer of the solid matter on the collection site.

17. The solid matter collection apparatus according to claim 1 further comprising:

a visualization reagent attached to the collection site.

18. The method according to claim 11 wherein analyzing the solid matter includes analyzing for a visualization agent.

* * * * *